United States Patent [19]

Peyman et al.

[11] Patent Number: 5,756,749

[45] Date of Patent: May 26, 1998

[54] PROCESS FOR THE PREPARATION OF 1-HYDROXY-2-PYRIDONES

[75] Inventors: Anuschirwan Peyman, Kelkheim; Dieter Bernd Reuschling, Butzbach; Adolf Heinz Linkies, Frankfurt, all of Germany

[73] Assignee: Hoechst Aktiengesellschaft, Frankfurt am Main, Germany

[21] Appl. No.: 552,068

[22] Filed: Nov. 2, 1995

[30] Foreign Application Priority Data

Nov. 2, 1994 [DE] Germany ............... 44 39 029.7
May 16, 1995 [DE] Germany ............... 195 17 891.2

[51] Int. Cl.$^6$ ..................................... C07D 213/08
[52] U.S. Cl. ........................................ 546/250; 546/290
[58] Field of Search ............................ 546/249, 290, 546/301, 250

[56] References Cited

U.S. PATENT DOCUMENTS

| | | | |
|---|---|---|---|
| 3,972,888 | 8/1976 | Lohaus et al. | 260/297 Z |
| 4,797,409 | 1/1989 | Lohaus et al. | 514/345 |
| 4,916,228 | 4/1990 | Reuschling et al. | 546/290 |
| 5,286,867 | 2/1994 | Lohaus et al. | 546/249 |

FOREIGN PATENT DOCUMENTS

| | | |
|---|---|---|
| 2214608 | 10/1973 | Germany. |
| 3626210 | 10/1987 | Germany. |

OTHER PUBLICATIONS

El-Kholy, I.E. et al, J. Chem. Soc. (London), 1961, pp. 4490–4498.

Wiley, R.H. et al, J. Am. Chem. Soc, 1956, vol. 78, pp. 2393–2398.

March, J., Advanced Organic Chemistry: Reactions, Mechanisms and Structure, 1992, 4th edition, Wiley & Sons, Inc., pp. 421–424.

*Primary Examiner*—C. Warren Ivy
*Assistant Examiner*—Garth M. Dahlen
*Attorney, Agent, or Firm*—Finnegan, Henderson, Farabow, Garrett & Dunner, L.L.P.

[57] ABSTRACT

The invention relates to a process for the preparation of 1-hydroxy-2-pyridones of the formula I

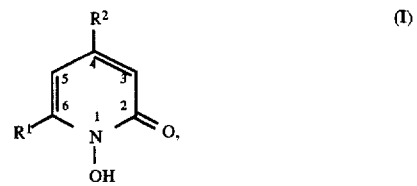

by reaction of a pyrone of the formula II

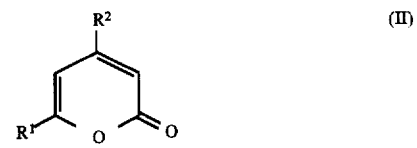

with a hydroxylammonium salt in the presence of basic compounds, which comprises carrying out the reaction in the presence of a distillable, filterable or extractable acid or a salt thereof in an amount of 0.01 to 20 equivalents with respect to the pyrone of the formula II, and employing as the basic compounds an alkali metal carbonate and/or alkali metal bicarbonate in an amount of 0.8 to 5 equivalents with respect to the hydroxylammonium salt, the radicals $R^1$ and $R^2$ in the formulae I and II are described herein.

5 Claims, No Drawings

PROCESS FOR THE PREPARATION OF 1-HYDROXY-2-PYRIDONES

1-Hydroxy-2-pyridones are prepared by the process described in DE 2,214,608 by reaction of the corresponding 2-pyrones (formula II) with hydroxylamine or one of its salts in the presence of an—optionally substituted—aminopyridine or imidazole. The aminopyridine or imidazole is advantageously employed here in at least the equimolar amount with respect to the hydroxylammonium salt. Temperatures between 50° C. and 120° C. are stated as the temperature range. During the reaction, the ring oxygen atom of the 2-pyrone is replaced by the N-OH group. The yields are between 60% and 70% of theory, based on the 2-pyrone employed. This process has the disadvantage that considerable amounts of the relatively valuable and expensive aminopyridines and/or imidazoles are used which, because of their considerable value and also for environmental protection reasons, must be recovered again. Furthermore, the process is very time-consuming.

1-Hydroxy-2-pyridones are prepared by the process described in DE 3,626,210 by reaction of the corresponding 2-pyrones with hydroxylamine or a hydroxylammonium salt in the presence of basic compounds, such as alkali metal carbonate or bicarbonate, at temperatures between 50° C. and 120° C., the alkali metal carbonate advantageously being employed here in at least the equimolar amount with respect to the hydroxylammonium salt. The increased profitability and the low environmental pollution are the advantage of this process compared with that described in DE 2,214,608. The lower yields compared with DE 2,214,608, which are between 50% and 60% of theory, based on the 2-pyrone employed, are a disadvantage of the process described in DE 3,626,210.

It has now been found that the amount of by-products of the process described in DE 3,626,210 is reduced by the reaction in the presence of a distillable, filterable or extractable acid or salt thereof such as ion exchangers, acetic acid or trifluoroacetic acid.

Trifluoroacetic acid in particular has the advantage that, owing to its low boiling point, it can be removed from the reaction mixture by distillation and can be reused. The economy of the process is increased without resulting in greater environmental pollution.

The invention relates to a process for the preparation of 1-hydroxy-2-pyridones of the formula I

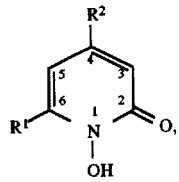

(I)

by reaction of a pyrone of the formula II

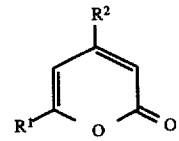

(II)

with a hydroxylammonium salt in the presence of basic compounds, which comprises carrying out the reaction in the presence of a distillable, filterable or extractable acid or a salt thereof in an amount of 0.01 to 20 equivalents with respect to the pyrone of the formula II, and employing as the basic compounds an alkali metal carbonate and/or alkali metal bicarbonate in an amount of 0.8 to 5 equivalents with respect to the hydroxylammonium salt, the radicals $R^1$ and $R^2$ in the formulae I and II having the following meanings:

$R^1$ is a branched or unbranched alkyl having 1 to 17 carbon atoms, preferably 1 to 12 carbon atoms, in particular 1 to 10 carbon atoms, a branched or unbranched alkenyl having 2 to 17 carbon atoms, a cycloalkyl having 3 to 8 carbon atoms in the ring, preferably 6 carbon atoms in the ring;

the cycloalkyl radical mentioned being unsubstituted or substituted by 1 to 3 alkyl radicals each having 1 to 3 carbon atoms, a phenyl, phenyloxy-($C_1$–$C_4$) alkyl or phenyl-($C_1$–$C_4$) alkyl radical which is unsubstituted or substituted in the aromatic nucleus by 1 to 3 ($C_1$–$C_6$)alkyl, benzyl, ($C_1$–$C_6$)alkoxy, phenoxy or halogen radicals, it also being possible for the benzyl or phenoxy group present as a substituent to be substituted in the same manner, and the cycloalkyl, phenyl, phenyloxy-($C_1$–$C_4$)alkyl or phenyl-($C_1$–$C_4$)alkyl radicals mentioned being bonded to the pyridone ring directly or via a methylene or ethylene group, and $R^2$ is a hydrogen atom, an alkyl having 1 to 6 carbon atoms, an alkenyl having 2 to 6 carbon atoms or a benzyl radical, the alkyl, alkenyl or benzyl radicals being unsubstituted or substituted in the manner described for $R^1$.

Among the radicals $R^1$ and $R^2$ which contain the phenyl radical, those in which this phenyl nucleus is unsubstituted or only mono- or disubstituted are preferred. Preferred radicals among those mentioned for $R^2$ are alkyl radicals having 1 to 4, in particular 1 to 2 carbon atoms, and preferred radicals among the alkenyl radicals are those having 2, 3, or 4 carbon atoms.

A compound of the formula I is especially preferably prepared; in it, $R^1$ is 2,4,4-trimethylpentyl, cyclohexyl or 4-(4-chlorophenoxy)-phenoxymethyl and $R^2$ is methyl.

The term halogen radical is understood as meaning a fluorine, chlorine, bromine or iodine atom. Alkyl means compounds which are derived, for example, from methane, ethane, propane, butane, pentane, hexane or heptane. The term alkenyl is understood as meaning compounds which are derived, for example, from ethene, propene, butene, pentene, hexene or heptene.

Examples of a distillable, filterable or extractable acid or a salt thereof which is employed in the process according to the invention are ion exchangers, acetic acid or trifluoroacetic acid. The addition of trifluoroacetic acid increases the yield of the process. The sodium salt or potassium salt are advantageously employed as the salt. 0.01 to 20 equivalents of trifluoroacetic acid, with respect to the pyrone of the formula II, are preferably employed, preferably 0.05 to 1 equivalents, in particular 0.1 to 0.3 equivalents.

The hydroxylammonium salt is employed in the equimolar amount with respect to the pyrone of the formula II; however, it can also be employed in excess in order to accelerate the reaction, better yields often then being obtained. It may also be expedient to add the hydroxylammonium salt in several portions in the course of the reaction. All salts of hyroxylamine, for example the chloride, the sulfate or the acetate, can essentially be used as the hydroxylammonium salt. However, it is preferable to carry out the reaction with the readily accessible hydroxylammonium sulfate.

An alkali metal carbonate or alkali metal bicarbonate are preferably employed as the basic compounds in the process according to the invention in an amount of 0.8 to 5 equivalents with respect to the hydroxylammonium salt, in particular 0.9 to 1.1 equivalents.

Possible alkali metal carbonates or alkali metal bicarbonates are virtually all the carbonates and bicarbonates of the alkali metals, for example $Li_2CO_3$, $Na_2CO_3$, $K_2CO_3$, $NaHCO_3$ and $KHCO_3$. The carbonates and bicarbonates of sodium and of potassium are preferred, and $Na_2CO_3$ is particularly preferred. The alkali metal carbonates and alkali metal bicarbonates can be employed either individually or in practically any mixture. Their amount is expediently at least equivalent to the amount of hydroxylammonium salt used, but if an excess of hydroxylammonium salt is used, a smaller amount of alkali metal carbonate or alkali metal bicarbonate can also be employed. For example, 0.5 mol of $Na_2CO_3$ or 1 mol of $NaHCO_3$ is to be used per mole of hydroxylammonium chloride.

To carry out the process according to the invention, the pyrone of the formula II is advantageously mixed with the hydroxylammonium salt, the alkali metal carbonate and the trifluoroacetic acid, and the resulting crystal slurry is heated until no pyrone of the formula II can be detected; after the inorganic salts and the trifluoroacetic acid has been removed, the pyridone of the formula I formed is isolated directly or, even better, as the salt of an organic base, for example as the ethanolamine salt. The process according to the invention is carried out at a temperature of 50° C. to 120° C., preferably 60° C. to 105° C.

It is also possible to add inert solvents or diluents. In general, however, this is not necessary but is preferred. Solvents or diluents are added in small amounts or in an amount of up to 50 percent by weight of the total reaction batch. The amount is preferably 3 to 15 percent by weight. The solvents or diluents can be polar or nonpolar and water-miscible or -immiscible. The following substances, for example, can be used:

water, low molecular weight alcohols, such as methanol, ethanol or isopropanol, ethylene glycol, ethylene glycol monomethyl ester, propylene glycol, acid amides, such as dimethylformamide, and esters, such as ethyl acetate, ethers, such as diisopropyl ether, chlorinated hydrocarbons, such as chlorobenzene, nitriles, such as acetonitrile, and hydrocarbons of an aliphatic, cycloaliphatic or aromatic nature, such as heptane or toluene.

The yields of the compound of the formula I achieved are as a rule 60% to 66%, based on the pyrone of the formula II.

The acid employed and the solvents which may be present can be removed from the reaction mixture by filtration, extraction or distillation and can be re-used in the process of the invention after purification if desired.

Compared with the process in DE 3,626,210, the process according to the invention is distinguished by higher yields, by less pollution of the environment and by higher profitability.

EXAMPLE 1

204.2 g (0.9 mol) of 4-methyl-6-(2,4,4-trimethylpentyl)-2-pyrone (98%), 179.4 g (2.56 mol) of hydroxylammonium chloride (99%) and 135.9 g (1.27 mol) of sodium carbonate (99%) are suspended in 200 ml of n-heptane and 2 ml of water, and 12.6 ml (0.16 mol) of trifluoroacetic acid are added. During this addition, severe evolution of $CO_2$ occurs. The reaction mixture is heated at 95° C. for 15 hours, while stirring. The mixture is allowed to cool and is extracted with 300 ml of 0.1N NaOH. Heptane and the trifluoroacetic acid which remains are distilled off under reduced pressure, the residue is dissolved in 400 ml of ethyl acetate, and 48.6 g (0.79 mol) of ethanolamine are added to the resulting solution at about 50° C. After seeding, the solution is allowed to cool. The crystals formed are filtered off with suction, washed with a little cold ethyl acetate and dried. The yield of 1-hydroxy-4-methyl-6-(2,4,4-trimethylpentyl)-2-pyridone (ethanolamine salt) is 169.3 g (63%).

EXAMPLE 2

204.2 g (0.9 mol) of 4-methyl-6-(2,4,4-trimethyl-pentyl)-2-pyrone (98%), 207.62 g (1.26 mol) of hydroxylammonium sulfate (99%) and 135.9 g (1.27 mol) of sodium carbonate (99%) are suspended in 200 ml of n-heptane and 2 ml of water, and 12.6 ml (0.16 mol) of trifluoroacetic acid are added, during which severe evolution of $CO_2$ occurs. The reaction mixture is heated at 95° C. for 15 hours, while stirring. Then 5 ml of water and 34 ml of concentrated $H_2SO_4$ are added. Heptane and trifluoroacetic acid are distilled off under reduced pressure, the residue is dissolved in 400 ml of ethyl acetate, and the solution is washed to neutrality with 1 N NaOH. Ethyl acetate and water are distilled off under reduced pressure. The residue is again dissolved in 400 ml of ethyl acetate, 55.25 g (0.90 mol) of ethanolamine are added to the solution at about 50° C., and the crystalline product is obtained as in Example 1. The yield of 1-hydroxy-4-methyl-6-(2,4,4-trimethylpentyl)-2-pyridone (ethanolamine salt) is 168.2 g (63%).

I claim:

1. A process for the preparation of a 1-hydroxy-2-pyridone of formula (I)

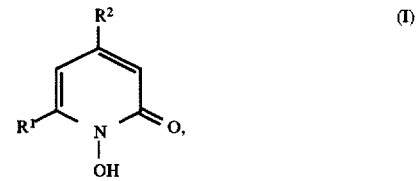

which comprises reacting a pyrone of formula (II)

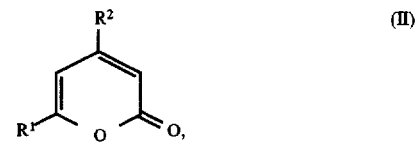

with a hydroxylammonium salt in the presence of basic compounds, wherein the reaction is carried out in the presence of trifluoroacetic acid or a salt thereof in an amount of 0.01 to 20 equivalents with respect to the pyrone of formula (II), and employing as the basic compounds an alkali metal carbonate and/or alkali metal bicarbonate in an amount of 0.8 to 5 equivalents with respect to the hydroxylammonium salt, the radicals $R^1$ and $R^2$ in the formulae (I) and (II) having the following meanings:

$R^1$ is a branched or unbranched alkyl having 1 to 17 carbon atoms, a branched or unbranched alkenyl having 2 to 17 carbon atoms, a cycloalkyl having 3 to 8 carbon atoms in the ring, the cycloalkyl being unsubstituted or substituted by 1 to 3 alkyl radicals each having 1 to 3 carbon atoms and being bonded to the pyridone ring directly or via a methylene or ethylene group, and $R^2$ is a hydrogen atom, an alkyl having from 1 to 6 carbon atoms, an alkenyl having 2 to 6 carbon atoms or a benzyl radical, the alkyl, alkenyl or benzyl radicals being unsubstituted or substituted in the manner described for $R^1$, wherein said 1-hydroxy-2-pyridone is obtained in at least 61% yield.

2. The process as claimed in claim 1, wherein the trifluoroacetic acid is employed in an amount of 0.05 to 1 equivalents with respect to the pyrone of the formula (II), and the alkali metal carbonates and/or alkali metal bicarbonates are employed as the basic compounds in an amount of 0.9 to 1.1 equivalents with respect to the hydroxylammonium salt.

3. The process as claimed in claim 1, wherein the sodium or potassium salt of trifluoroacetic acid is employed as the acid.

4. The process as claimed in claim 2 wherein trifluoroacetic acid is employed in an amount of 0.1 to 0.3 equivalents with respect to the pyrone of formula (II).

5. The process as claimed in claim 4 wherein the sodium or potassium salt of trifluoroacetic acid is employed as the acid.

\* \* \* \* \*